United States Patent
Maj

(12) 
(10) Patent No.: US 6,255,329 B1
(45) Date of Patent: *Jul. 3, 2001

(54) COMBINED USE OF PRAMIPEXOLE AND SERTRALINE FOR THE TREATMENT OF DEPRESSION

(75) Inventor: Jerzy Maj, Kracau (PL)

(73) Assignee: Boehringer Ingelheim Pharma KG, Ingelheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/348,591

(22) Filed: Jul. 6, 1999

(30) Foreign Application Priority Data

Jul. 7, 1998 (DE) .............................. 198 30 201

(51) Int. Cl.⁷ ....................... A61K 31/425; A61K 31/135
(52) U.S. Cl. ............................. 514/367; 514/647
(58) Field of Search .................... 514/367, 647

(56) References Cited

U.S. PATENT DOCUMENTS

| | | | | |
|---|---|---|---|---|
| 4,536,518 | * | 8/1985 | Welch et al. | 514/647 |
| 4,843,086 | * | 6/1989 | Griss et al. | 514/367 |
| 4,886,812 | * | 12/1989 | Griss et al. | 514/321 |
| 4,962,128 | * | 10/1990 | Doogan et al. | 514/647 |
| 5,248,699 | * | 9/1993 | Sysko et al. | 514/647 |
| 6,191,153 | * | 2/2001 | Hammer et al. | 514/367 |

OTHER PUBLICATIONS

Maj et al Eur. J. Pharmacol. 324(1):31–37 Pra Antipsychotic & Sulpiride, 1997.*
Ferrari et al Psychopharmacology(Berlin) 113(2):172–176 Pra & Sulpiride, 1993.*
Carter et al Eur. J. Pharmacol. 200(1):65–72 Pra & Sulpiride, 1991.*
Borsini et al Psychopharmacology (Berlin) 97(2):183–188 Forced Swimming Test Discovers Antidepressant Activity, 1989.*
Piercey et al Clinical Neuropharmacology 18 Suppl. 1 534–542 Pra & Quinpirole, 1995.*
Willner Psycyhopharmacology 83(1):1–16 Learned Helplessness Test for Antidepress, 1984.*
Borsini et al Psychopharmacology 94(2):147–160 FST in Rats, not Mice Detects Antidepressants, 1988.*
Skrebuhhova et al Methods & Findings Exp. Clin. Pharmacol. 21(3):173–178 FST 4, 1999.*
Harkin et al Eur. J. Pharmacol. 364 2–3 123–132 Sertraline FST, Jan. 1999.*
J. Maj, Z. Rogoz, G. Skuza & K. Kolodziejczyk; "Antidepressant Effects Of Pramipexole, A Novel Dopamine Receptor Agonist"; Journal of Neural Transmission; Aug. 6, 1997; pp. 525–533; vol. 104; Pub. Springer–Verlag; Austria.
J. Maj, Z. Rogoz, G. Skuza & K. Kolodziejczyk; "Pramipexole Given Repeatedly Increases Responsiveness Of Dopamine D2 and D3 Receptors"; Abstrac—XIIIth International Congress Of Pharmacology; Jul. 26–31, 1998; Poster Topic p. 35; Germany.
O. Benkert, G. Gruender & H. Wetzel; "Dopamine Autoreceptor Agonists In The Treatment of Schizophrenia and Major Depression*"; Review—Pharmacopsychiatry; Nov. 1992; Review pp. 254–260; Georg Thieme Verlag Stuttgart; Germany.

* cited by examiner

*Primary Examiner*—Shep K. Rose
(74) *Attorney, Agent, or Firm*—R.P. Raymond; T. X. Witkowski; A. R. Stempel

(57) ABSTRACT

The present invention relates to the use of 2-amino-4,5,6,7-tetrahydro-6-n-propylamino-benzothiazole (pramipexole), the (+)- or (−)- enantiomer thereof, or one of the pharmacologically acceptable salts thereof, in conjunction with sertraline for the improved treatment of depression and depressive states.

19 Claims, No Drawings

COMBINED USE OF PRAMIPEXOLE AND SERTRALINE FOR THE TREATMENT OF DEPRESSION

FIELD OF THE INVENTION

The present invention relates to an agent with an antidepressant activity containing 2-amino-4,5,6,7-tetrahydro-6-n-propylamino-benzothiazole, the (+) or (−) enantiomer thereof, the pharmacologically acceptable acid addition salts thereof and a conventional antidepressant. The combination of pramipexole and sertraline is of particular interest.

BACKGROUND OF THE INVENTION

Pramipexole—(−)-2-amino-6-n-propylamino-4,5,6,7-tetrahydrobenzo-thiazole—is a dopamine-$D_3/D_2$ agonist, the synthesis of which is described in European Patent 186 087 and U.S. Pat. No. 4,886,812. Pramipexole is known primarily for treating schizophrenia and particularly for the treatment of Parkinson's disease. German Patent Application DE 38 43 227 discloses that pramipexole lowers the prolactin serum level, and it is also known from German Patent Application DE 39 33 738 to use pramipexole to lower high TSH levels. Its transdermal administration is disclosed in U.S. Pat. No. 5,112,842, and WO Patent Application PCT/EP93/03389 describes the use of pramipexole as an antidepressant.

Details of the preparation of the title compound can be found in EP-A 85 116 016, and reference is hereby made specifically to the literature cited therein.

DESCRIPTION OF THE INVENTION

It has now been found that, surprisingly, pramipexole, the (+) or (−) enantiomer thereof, or the pharmacologically acceptable acid addition salts thereof, combined with another antidepressant has a significantly greater antidepressant activity than either of the two individual components taken alone. The fact that the combination of active substances takes effect immediately should be particularly emphasised.

The improvement in the effect of pramipexole by the simultaneous administration of another antidepressant was discovered by administering to rats a combination of pramipexole and sertraline and then subsequently testing them according to the so-called "forced swimming test". Details of this test method can be found, for example, in Willner, Psychopharmacology 83, 1–16 (1984) or Borsini and Meli, Psychopharmacology 94, 147–160 (1988).

For the particular preferred combination of pramipexole and sertraline, (1S-cis)-4-(3,4-dichlorophenyl)-1,2,3,4-tetrahydro-N-methyl-1-naphthalenamine, their acid addition salts respectively, the test was carried out as follows. The animals were divided up into different groups and each group was given either a saline solution, a therapeutically effective amount of pramipexole, a therapeutic amount of sertraline or a combined dose of both antidepressants in the same therapeutic amount as the animals that received only one of the two active substances.

The combination of 2-amino-4,5,6,7-tetrahydro-6-n-propyl-amino-benzothiazole, the (+) or (−)-enantiomer thereof, the acceptable acid addition salts thereof and (1 S-cis)-4-(3,4-dichlorophenyl)-1,2,3,4-tetrahydro-N-methyl-1-naphthalenamine (sertraline) and the acid addition salts thereof is particularly preferred, while the combination of pramipexole and sertraline in the form of their hydrochlorides is most particularly preferred.

The invention also encompasses the combined use of pramipexole with antidepressants other than sertraline. Preferably these other antidepressants are selected from the following known compounds: alprazolam, chlordiazepoxide, clomipramine, chinpirol, dibenzepin, doxepin, fluvoxamine, lofepramine, maprotiline, mirtazapine, mianserin, moclobemide, nefazodone, nortriptyline, opipramol, paroxetine, sertraline, sulpiride, tranylcypromine, trazodone, trimipramine, tryptophan, venlafaxine and viloxazine.

The term "combination" for the purposes of the invention refers to either the co-administration of pramipexolc and the second antidepressant agent (with both agents being administered separately, but such that both agents will exert their therapeutic in concert) or to the administration of both agents together, as components of a single pharmaceutical dosage form.

Orally administered pharmaceutical formulations for pramipexole are known from the prior art and are obtainable in the German and U.S. markets.

The individual active substances may also be packaged in kit form as a combined pack of the individual drugs, as well as separately.

The combination of pramipexole and another antidepressant may be formulated analogously to conventional pharmaceutical preparations, generally together with a pharmaceutical carrier. In other words, an effective dose of the individual components and optionally a pharmaceutical carrier are formulated as plain or coated tablets, lozenges, powders, solutions, suspensions, emulsions, syrups, suppositories etc. For pramipexole the pharmaceutically effective dose per patient is between 0.01 and 10 mg, preferably between 0.08 and 5 mg.

The therapeutically effective doses of the second antidepressant in the combination are given in the Table which follows.

| Alprazolam | (25–100 mg) | Nefazodone | (100–300 mg) |
|---|---|---|---|
| Chlordiazepoxide | (5 mg) | Nortriptyline | (10–25 mg) |
| Clomipramine | (10–25 mg) | Opipramol | (50 mg) |
| Chinpirol | (1–5 mg) | Paroxetin | (20 mg) |
| Dibenzepin | (10–250 mg) | Sertraline | (50 mg) |
| Doxepin | (5–50 mg) | Sulpiride | (50–200 mg) |
| Fluvoxamine | (50–100 mg) | Tranylcypromine | (10 mg) |
| Lofepramine | (35–75 mg) | Trazodone | (25–100 mg) |
| Maprotiline | (10–75 mg) | Trimipramine | (25–250 mg) |
| Mianserin | (10–30 mg) | Tryptophan | (500 mg–2.5 g) |
| Mirtazapine | (30 mg) | Venlafaxine | (30–75 mg) |
| Moclobemide | (150–300 mg) | Viloxazine | (100 mg) |

In the combination according to the invention the recommended dose may in individual cases be below the single dose previously recommended for the monopreparation.

DESCRIPTION OF THE EXPERIMENTS

Pramipexole was used in doses of 0.1 and 0.3 mg/kg. In addition, trials were carried out using 0.05 mg/kg pramipexole. Sertraline was used in doses of 5 and 10 mg/kg as mentioned in the Tables. The tests were carried out on rats (male Wistar, 250–270 g) at RT while maintaining a natural day-night rhythm. Pramipexole (HCl) was dissolved in a physiological saline solution and sertraline (HCl) was dissolved in distilled water, and both substances were injected in a volume of 2 ml/kg.

Forced Swimming Test in Rats

The total immobility time was determined according to Porsolt et al. (1978) within a five-minute observation period.

Pramipexole (0.05, 0.1 and 0.3 mg/kg) and sertraline (5 or 10 mg/kg) were given three times at intervals of 24 hours, 5 hours and 1 hour before the test.

In separate groups pramipexole was also injected three times in the abovementioned dosage together with sertraline (5 or 10 mg/kg) as described above. Each group consisted of 10 rats.

Results

Pramipexole—0.1 mg/kg—does not alter the immobility time in the forced swimming test, whereas higher doses (0.3 mg) bring about a significant reduction in the immobility time.

A dosage of 5 mg/kg sertraline on its own likewise does not reduce the immobility time. However, the joint administration of 5 mg/kg of sertraline and 0.1 mg/kg of pramipexole noticeably reduces the immobility time. This effect is considerably more marked at higher doses of sertraline.

Sertraline alone in a dose of 10 mg/kg was inactive in the forced swimming test, but given in conjunction with pramipexole (0.1, 0.3 mg/kg). This effect is increased at higher doses of pramipexole. Pramipexole in a dosage of 0.05 mg/kg shows no effect on the immobility time but there is a reduction in the immobility time when it is combined with sertraline.

These results demonstrate the unexpected synergistic effect of pramipexole in conjunction with sertraline as an antidepressant.

TABLE 1

Effect of pramipexole (0.1 and 0.3 mg/kg) on its own or in conjunction with sertraline (5 mg/kg) on the immobility time in the forced swimming test in rats.

| Compounds | Immobility time(s) | |
|---|---|---|
| (mg/kg) | mean ± SEM | P |
| 1. carrier | 239.9 ± 3.1 | — |
| 2. sertraline 5 | 257.0 ± 7.0 | ns vs 1 |
| 3. pramipexole 0.1 | 223.4 ± 6.2 | ns vs 1 |
| 4. pramipexole 0.3 | 171.5 ± 9.2 | <0.001 vs 1 |
| 5. sertraline 5 + pramipexole 0.1 | 96.1 ± 10.3 | <0.001 vs 3 |
| 6. sertraline 5 + pramipexole 0.3 | 18.1 ± 3.5 | <0.001 vs 4 |

Pramipexole (0.1 or 0.3 mg/kg s.c.) and sertraline (5 mg/kg i.p.) are administered three times (24 hours, 5 hours and 1 hour) before the test.

TABLE 2

Effect of pramipexole (0.1 and 0.3 mg/kg) on its own or in conjunction with sertraline (10 mg/kg) on the immobility time in the forced swimming test in rats.

| Compounds | Immobility time(s) | |
|---|---|---|
| (mg/kg) | mean ± SEM | P |
| 1. carrier | 237.9 ± 2.7 | — |
| 2. sertraline 10 | 223.6 ± 9.9 | Ns vs 1 |
| 3. pramipexole 0.1 | 212.5 ± 6.9 | Ns vs 1 |
| 4. pramipexole 0.3 | 142.9 ± 7.9 | <0.001 vs 1 |
| 5. sertraline 10 + pramipexole 0.1 | 133.3 ± 6.9 | <0.001 vs 3 |
| 6. sertraline 10 + pramipexole 0.3 | 11.8 ± 2.3 | <0.001 vs 4 |

Pramipexole (0.1 or 0.3 mg/kg s.c.) and sertraline (10 mg/kg i.p.) are administered 3 times (24 hours, 5 hours and 1 hour) before the test.

TABLE 3

Effect of pramipexole (0.05 mg/kg) on its own or in conjunction with sertraline (5 and 10 mg/kg) on the immobility time in the forced swimming test in rats.

| Compounds | Immobility time(s) | |
|---|---|---|
| (mg/kg) | mean ± SEM | P |
| 1. carrier | 235.3 ± 4.8 | — |
| 2. pramipexole 0.05 | 245.5 ± 7.8 | ns vs 1 |
| 3. sertraline 5 | 247.5 ± 3.0 | ns vs 1 |
| 4. sertraline 10 | 223.7 ± 2.8 | ns vs 1 |
| 5. sertraline 5 + pramipexole 0.05 | 187.7 ± 11.2 | <0.001 vs 2 |
| 6. sertraline 10 + pramipexole 0.05 | 163.9 ± 10.0 | <0.001 vs 2 |

Pramipexole (0.05 mg/kg s.c.) and sertraline (5 and 10 mg/kg i.p.) are administered 3 times (24 hours, 5 hours and 1 hour) before the test.

What is claimed is:

1. A pharmaceutical composition comprising an antidepressive amount of 2-amino-4,5,6,7-tetrahydro-6-n-propylaminobenzothiazole, or a pharmaceutically acceptable acid addition salt thereof, and an antidepressive amount of sertraline or a pharmaceutically acceptable salt thereof.

2. A pharmaceutical composition in accordance with claim 1 comprising the (+)-enantiomer of 2-amino-4,5,6,7-tetrahydro-6-n-propylaminobenzothiazole, or a pharmaceutically acceptable acid addition salt thereof.

3. A pharmaceutical composition in accordance with claim 1 comprising the (−)-enantiomer of 2-amino-4,5,6,7-tetrahydro-6-n-propylaminobenzothiazole, or a pharmaceutically acceptable acid addition salt thereof.

4. A pharmaceutical composition in accordance with claim 1 comprising 2-amino-4,5,6,7-tetrahydro-6-n-propylaminobenzothiazole dihydrochloride or the monohydrate thereof.

5. A pharmaceutical composition in accordance with claim 1 comprising of 0.05–10 mg of 2-amino-4,5,6,7-tetrahydro-6-n-propylaminobenzothiazole, (−)-2-amino-4,5,6,7-tetrahydro-6-n-propylaminobenzothiazole, or (−)-2-amino-4,5,6,7-tetrahydro-6-n-propylaminobenzothiazole dihydrochloride monohydrate.

6. A pharmaceutical composition in accordance with claim 1 comprising 0.88–1.5 mg of 2-amino-4,5,6,7-tetrahydro-6-n-propylaminobenzothiazole, (−)-2-amino-4,5,6,7-tetrahydro-6-n-propylaminobenzothiazole, or (−)-2-amino-4,5,6,7-tetrahydro-6-n-propylaminobenzothiazole dihydrochloride or the monohydrate thereof.

7. A pharmaceutical composition in accordance with claim 1 comprising 0.88–1.1 mg of (−)-2-amino-4,5,6,7-tetrahydro-6-n-propylaminobenzothiazole, or between 0.125 and 1.5 mg of (−)-2-amino-4,5,6,7-tetrahydro-6-n-propylaminobenzothiazole dihydrochloride or the monohydrate thereof.

8. A pharmaceutical composition in accordance with claim 1, 2, 3, 4, 5, 6 or 7 comprising between 25 and 200 mg of sertraline.

9. A pharmaceutical composition in accordance with claim 8 comprising 50 mg of sertraline.

10. A method for treating depression which comprises administering an antidepressive amount of 2-amino-4,5,6,7-tetrahydro-6-n-propylaminobenzothiazole, or a pharmaceutically acceptable acid addition salt thereof, and an antidepressive amount of sertraline or a pharmaceutically acceptable salt thereof.

11. The method of claim 10 wherein the (+)-enantiomer of 2-amino-4,5,6,7-tetrahydro-6-n-propylaminobenzothiazole, or a pharmaceutically acceptable acid addition salt thereof is administered.

12. The method of claim 10 wherein the (−)-enantiomer of 2-amino-4,5,6,7-tetrahydro-6-n-propylaminobenzothiazole, or a pharmaceutically acceptable acid addition salt thereof is administered.

13. The method of claim 10 wherein 2-amino-4,5,6,7-tetrahydro-6-n-propylaminobenzothiazole dihydrochloride is administered.

14. The method of claim 10 wherein 2-amino-4,5,6,7-tetrahydro-6-n-propylaminobenzothiazole dihydrochloride monohydrate is administered.

15. The method of claim 10 wherein 0.05–10 mg of 2-amino-4,5,6,7-tetrahydro-6-n-propylaminobenzothiazole, (−)-2-amino-4,5,6,7-tetrahydro-6-n-propylaminobenzothiazole, or (−)-2-amino-4,5,6,7-tetrahydro-6-n-propylaminobenzothiazole dihydrochloride monohydrate is administered.

16. The method of claim 10 wherein 0.88–1.5 mg of 2-amino-4,5,6,7-tetrahydro-6-n-propylaminobenzothiazole, (−)-2-amino-4,5,6,7-tetrahydro-6-n-propylaminobenzothiazole, or (−)-2-amino-4,5,6,7-tetrahydro-6-n-propylaminobenzothiazole dihydrochloride monohydrate is administered.

17. The method of claim 10 wherein 0.88–1.1 mg of (−)-2-amino-4,5,6,7-tetrahydro-6-n-propylaminobenzothiazole, or between 0.125 and 1.5 mg of (−)-2-amino-4,5,6,7-tetrahydro-6-n-propylaminobenzothiazole dihydrochloride monohydrate is administered.

18. The method of claim 10, 11, 12, 13, 14, 15 or 16 wherein between 25 and 200 mg of sertraline is administered.

19. The method of claim 10 wherein 50 mg of sertraline is administered.

* * * * *

UNITED STATES PATENT AND TRADEMARK OFFICE
CERTIFICATE OF CORRECTION

PATENT NO. : 6,255,329 B1
DATED : July 3, 2001
INVENTOR(S) : Jerzy Maj

It is certified that error appears in the above-identified patent and that said Letters Patent is hereby corrected as shown below:

Title page,
Item [56], References Cited, OTHER PUBLICATIONS, "Psycyhopharmacology" should read -- Psychopharmacology --.

Column 2,
Line 12, "pramipexolc" should read -- pramipexole --

Signed and Sealed this

First Day of April, 2003

JAMES E. ROGAN
*Director of the United States Patent and Trademark Office*